(12) United States Patent
Weber

(10) Patent No.: US 7,378,395 B2
(45) Date of Patent: May 27, 2008

(54) MUTANTS OF BONE MORPHOGENETIC PROTEINS

(75) Inventor: Franz Weber, Singen (DE)

(73) Assignee: The University of Zurich, Zurich (CH)

(*) Notice: Subject to any disclaimer, the term of this patent is extended or adjusted under 35 U.S.C. 154(b) by 0 days.

(21) Appl. No.: 11/452,550

(22) Filed: Jun. 14, 2006

(65) Prior Publication Data
US 2006/0270602 A1 Nov. 30, 2006

Related U.S. Application Data

(62) Division of application No. 10/225,506, filed on Aug. 21, 2002, now Pat. No. 7,186,689.

(30) Foreign Application Priority Data
Aug. 24, 2001 (FI) .................................. 20011705

(51) Int. Cl.
*A61K 38/00* (2006.01)
*A61K 38/18* (2006.01)
(52) U.S. Cl. ........................................ 514/12; 530/399
(58) Field of Classification Search ..................... None
See application file for complete search history.

(56) References Cited

U.S. PATENT DOCUMENTS 7,186,689 B2* 3/2007 Weber .......................... 514/12

FOREIGN PATENT DOCUMENTS

| WO | WO 99/61611 | 12/1999 |
|----|-------------|---------|
| WO | WO 00/17360 | 3/2000  |
| WO | WO 00/20449 | 4/2000  |
| WO | WO 01/11041 | 2/2001  |

OTHER PUBLICATIONS

Wozney et al., Science. Dec. 16, 1988;242(4885):1528-1534.*
Information Hyperlinked Over Proteins, BMP4.*
Barlow et al., Development. Jan. 1997;124(2):391-8, Abstract Only.*
Jane et al., Mol Ther. Oct. 2002;6(4):464-70, Abstract Only.*
Kishimoto et al., Bone. Aug. 2002;31(2):340-7, Abstract Only.*
Weber et al., J Bone Miner Res. Dec. 2003;18(12):2142-51.*
Wilde et al., Drugs. Oct. 1997;54(4):597-614.*
Calin et al., Eds., The Spondylarthritides. Oxford University Press. New York. 1998. pp. 27-30.*
O'Connor et al., Clin Orth and Rel Res. 1998;346:71-80.*
Karsenty et al., Genes Dev. Dec. 1, 1999;13(23):3037-51.*
Baysal et al., Eur Radiol. 1998;8(3):479-81.*
Kirsch et al., "BMP-2 Antagonists Emerge from Alterations in the Low-Affinity Binding Epitope for Receptor BMPR-II," 19(13):3314-3324, 2000.
Marker et al. "Spectrum of Bmp5 Mutations from Germline Mutagenesis Experiments in Mice," *Genetics*, 145(2):435-443, 1997.
Ngo et al., "Computational Complexity, Protein Structure Prediction, and the Levinthal Paradox," *The Protein Folding Problem and Tertiary Structure Prediction*, Merz et al., Eds., Birkhauser, Boston, MA, (1994) pp. 433-506.
Nickel et al., "The Crystal Strucutre of the BMP-2:BMPR-IA Complex and the Generation of BMP-2 Antagonists," *J. Bone and Joint Surgery*, 83-A(Supp. 1)(No. Pt. 1):S7-14, 2001.
Gelbart, "The decapentaplegic gene: a TGF-beta homologue controlling pattern formation in Drosophila," *Development*, 107 Suppl:65-74 (1989).
Scheufler et al., "Crystal Structure of Human Bone Morphogenetic Protein-2 at 2.7 Å Resolution," *J. Mol. Biol.*, 287:103-115 (1999).
Weber et al., "Disulfide Bridge Conformers of Mature BMP Are Inhibitors for Heterotopic Ossification," *Biochem. and Biophys. Res. Comm.*, 286:554-558 (2001).
Wolring et al., "Mutations at the GABA receptor selectivity filter: a possible role for effective charges," *J. Physiol.* 548(2):527-540 (2003).
Wozney et al., "Novel Regulators of Bone Formation: Molecular Clones and Activities," *Science*, 242(4885):1528-1534 (1988).
Wozney, "Bone Morphogenetic Proteins," *Progress in Growth Factor Research*, 1:267-280 (1989).
Jelic et al., "Regeneration of Articular Cartilage Chondral Defects by Osteogenic Protein-1 (Bone Morphogenetic Protein-7) in Sheep," *Growth Factors*, 19:101-113 (2001).
Kirker-Head, "Potential applications and delivery strategies for bone morphogenetic proteins," *Advanced Drug Delivery Reviews*, 43:65-92 (2000).
Simic et al., "Systemically Administered Bone Morphogenetic Protein-6 Restores Bone in Aged Ovariectomized Rats by Increasing Bone Formation and Suppressing Bone Resorption," *J. Biol. Chem.*, 281(35):25509-25521 (2006).
Urist, "Experimental Delivery Systems for Bone Morphogenetic Protein," *Encyclopedic Handbook of Biomaterials and Bioengineering*, Wise et al. (eds.), vol. 2, Part A: Materials, pp. 1093-1133 (1995).
Weber et al., "Slow and continuous application of human recombinant bone morphogenetic protein via biodegradable poly(lactide-co-glycolide) foamspheres," *Int. J. Oral Maxillofac. Surg.*, 31:60-65 (2002).

* cited by examiner

*Primary Examiner*—Manjunath Rao
*Assistant Examiner*—Cherie Woodward
(74) *Attorney, Agent, or Firm*—Banner & Witcoff, Ltd.

(57) ABSTRACT

The present invention relates to novel mutants of bone morphogenetic proteins (BMPs) useful as inhibitors of heterotopic ossification. Specifically, the present invention related to novel mutants containing only the entire region involved in the formation of finger 2 including the wrist epitope of a BMP with a specific cysteine residue or specific cysteine residues replaced by a different amino acid. The present invention also relates to pharmaceutical compositions containing these mutants and to methods for using the mutants and pharmaceutical compositions in therapy.

12 Claims, 3 Drawing Sheets
(1 of 3 Drawing Sheet(s) Filed in Color)

MUTANTS OF BONE MORPHOGENETIC PROTEINS

RELATED APPLICATION(S)

This application is a division of U.S. patent application Ser. No. 10/225,506, filed Aug. 21, 2002, issued on Mar. 7, 2007 as U.S. Pat. No. 7,186,689; which claims priority from Finnish patent application FI 20011705, filed Aug. 24, 2001; each of which are hereby incorporated by reference in its entirety.

FIELD OF THE INVENTION

The present invention relates to novel mutants of bone morphogenetic proteins (BMPs) useful as inhibitors of heterotopic ossification. Specifically, the present invention relates to novel mutants containing only the entire region involved in the formation of finger 2 including the wrist epitope of a BMP with a specific cysteine residue or specific cysteine residues replaced by a different amino acid. The present invention also relates to pharmaceutical compositions containing these mutants and to the use of the mutants and pharmaceutical compositions in therapy.

BACKGROUND OF THE INVENTION

Heterotopic ossification (HO) is a frequent complication in patients who have suffered head and neck traumas, traumatic acetabular fracture, or undergone total hip replacement. It is a process of bone formation at ectopic sites, such as muscle and connective tissue, that can lead to decreased mobility, pain, or even total ankylosis, predominantly in hip and elbow joints (for review see: Eulert, J., et al., *Der Unfallchirurg* 100 (1991) 667-674; Nilsson, O. S., *Acta Orthop. Scand.* 69 (1998) 667-674). As the number of elderly people increases and, subsequently, the number of the total hip arthoplastic operations rises, the number of patients suffering from HO can be expected to grow. HO is also manifested in some inherited diseases, such as fibrodysplasia, or acquired bone forming lesions, such as spinal hyperostosis, myelopathy and spondylitis ankylosans, in which no curable treatment is available or a surgical operation is the only means of treatment.

Effective prevention of the formation of extra bone following total hip replacement is needed in about 10 to 50% of patients (Seegenschmiedt, M. H., et al., *Int'l. J. Radiation Oncology Biol. Phys.* 39 (1997) 161-171) and presently radiotherapy, non-steroidal anti-inflammatory drugs or both are being used for prevention (Coventry M. B. and Scanion P. W., *J. Bone Joint Surg.* 63 (1981) 201-208; Dahl, H. K., in *Symposium on Arthrose*, Ed. MSD Blinderm, Norway 1975, pp. 37-46). Unfortunately, these treatments are associated with potential side effects, which restrict their application to high-risk patients only (Nielsson, O. S., supra).

A group of proteins, designated as bone morphogenetic proteins (BMPs), which occur naturally as dimers, play a key role in any ossification process. The BMP-family is divided to subfamilies including the BMPs, such as BMP-2 and BMP-4, osteogenic proteins (OPs), such as OP-1 or BMP-7, OP-2 or BMP-8, BMP-5, BMP-6 or Vgr-1, cartilage-derived morphogenetic proteins (CDMPs), such as CDMP-1 or BMP-14 or GDF-5, growth/differentiation factors (GDFs), such as GDF-1, GDF-3, GDF-8, GDF-9, GDF-11 or BMP-11, GDF-12 and GDF-14, and other subfamilies, such as BMP-3 or osteogenin, BMP-9 or GDF-2, and BMP10. The BMP-family with more than thirty members belongs to the TGF-β-super-family (Reddi, H., *Cytokine & Growth Factor Reviews* 8 (1997) 11-20).

The overall folding topology of the BMP-family members and other members of the TGF-β super-family, for which the 3-dimentional structure has been determined, resembles a hand exhibiting the victory sign, with the wrist representing the central alpha-helix, two fingers, two anti-parallel β-sheets, and the palm the cysteine-knot region (Scheufeler, C. et al., *J. Mol. Biol.* 287 (1999) 103-115). The cysteine-knot consists of three intrachain disulfide bridges and is the main stabilizer of the 3-D structure, and it is so effective that the biological activity is preserved even after extensive exposure to low pH, urea or guanidine hydrochloride treatments (Sampath, T. K., and Reddi, A. H., *Proc. Natl. Acad. Sci. USA* 78 (1981) 7599-7603). Further stabilization of the topology is achieved by the dimerization of two monomers, creating an internal hydrophobic core (Scheufeler, C. et al., supra). The overall dimeric structure is also necessary for the biological action, such as osteoinduction, as it enables the simultaneous binding of a dimeric molecule to the corresponding receptor, for instance the simultaneous binding of a BMP-dimer to a type I and a type II serine/threonine receptor, forming a heterotetramer which triggers a signal cascade via the phosphorylation of Smads (Kawabata, M. et al., *Cyto & Growth Factor Rev.* 9 (1998) 49-61; Massaqué, *Annu. Rev. Biochem.* 67 (1998) 753-791). Recently, it has been shown that BMP-2 dimers can exist as two biological distinct folding variants, an osteoinductive (os)BMP-2 and an osteoinhibitive (inh)BMP-2, which differ only in their disulfide bridge composition (Weber, F., et al., *Biochem. Biophys. Res. Commun.* 286 (2001) 554-558).

Results based on the protein and nucleotide sequences of the BMPs have revealed that the morphogenesis of bone, comprising chemotaxis, mitosis, and differentiation, is governed by the action of the BMPs. It has also been shown that the effects of the BMPs are not limited to bone and cartilage. In the early stage of embryogenesis the BMPs rule the formation of the entire body plan and specify the tissue types and axes. In an adult, the BMPs affect to the ability of bones to repair successfully (for review, see Wozney, J. and Rosen, V., *Clin. Orthop. Rel. Res.* 346 (1998) 26-37). This aspect of the BMP action together with its osteoinductive power suggests the use the BMPs in the treatment of patients for the enhancement of fracture healing and the augmentation of bone. Another aspect of the BMPs is their interaction in the manifestation of heterotopic ossification, which has created expectations to develop inhibitors of the BMPs and use them as therapeutic agents in HO.

BMP mutants lacking the ability to form the correct disulfide bond have been disclosed in Finnish Patent Application 20011478. Osteoinhibitory recombinant BMP-4 mutants spanning amino acids 48 to 116 of the 116 amino acids of the mature BMP-4 (Sequence Id. No. 2), i.e. covering the entire region involved in the formation of finger 2 plus the wrist epitope but not that of finger 1 (mutant 1), and BMP-4 mutants spanning amino acids 1 to 55 (mutant 2) or 1 to 88 (mutant 3), i.e. containing only the region for finger I, but not finger 2, are exemplified in said application. The cysteine responsible for dimerization is located at position 80 and is therefore present in mutants 1 and 3. The cysteine residues involved in the formation of the cysteine-knot are at positions 16, 45, 49, 81, 113 and 115 and accordingly, none of the mutants is capable of forming the entire cysteine-knot structure. It was found that mutant 1, but not mutants 2 or 3, was able to reduce alkaline phosphatase activity in MC3T3 E1 cells, while the presence or absence of cysteine 80, which is involved in dimer formation, did not correlate with the cellular response. It was therefore concluded that the amino acid sequence responsible for the inhibition of ossification resides in the C-terminal half of mature BMP, the region where an anti-parallel B-sheet, adopting a twisted crossover conformation plus the wrist, epitope form finger 2.

Additional and more effective inhibitors of the BMPs useful in the treatment of heterotopic ossification are still needed.

A purpose of the present invention is to provide additional novel means for the utilization of the bone forming inhibitory activity of the BMPs and other members of the TGF-β super-family, where applicable, in the treatment of patients in orthopaedics and other fields in medicine.

Specifically, a purpose of the present invention is to provide novel BMP mutants that would be useful in the treatment and prevention of heterotopic ossification and other diseases involving undesired bone formation. Such mutants would significantly add to the options that now are available in the treatment of HO, and would lack the side effects of the non-steroidal anti-inflammatory drugs (NSAIDs) and the radiotherapy, which at present are the alternative methods of treatment.

SHORT DESCRIPTION OF THE INVENTION

The present invention provides novel BMP mutants or mutants of other members of the TGF-β super-family, where applicable, such as BMP-4 mutants, which are capable of effectively inhibiting heterotopic ossification. Specifically, the present invention provides novel mutants consisting essentially of only the region involved in the formation of finger 2 including the wrist epitope of the mature BMP sequence with specific cysteine residues replaced by a different amino acid.

The present invention also provides pharmaceutical compositions containing such mutants in a suitable pharmaceutical carrier.

The present invention relates to mutants of bone morphogenetic protein (BMP) or another member of the TGF-β super-family, where applicable, consisting essentially of the region involved in the formation of finger 2 including the wrist epitope, in which a specific cysteine residue or specific cysteine residues have been replaced by a different amino acid, preferably a neutral amino acid.

Specifically, the present invention relates to mutants of BMPs, such as BPM-2 and BMP-4, consisting essentially of the region involved in the formation of finger 2 including the wrist epitope, in which a specific cysteine residue or specific cysteine residues have been replaced by a different amino acid, preferably a neutral amino acid, such alanine.

In particular, the present invention relates to mutants of BMP-4 consisting essentially of the region involved in the formation of finger 2 including the wrist epitope, i.e. amino acids 48 to 116 of the mature BMP-4 sequence, in which a specific cysteine residue, preferably that at position 115, has been replaced by a different amino acid, preferably by a neutral amino acid, most preferably by an alanine residue.

The present invention also relates to pharmaceutical compositions comprising such BMP mutants in a suitable pharmaceutical carrier.

The present invention further relates to the use of such mutants in therapy, especially in therapy in the field of orthopaedics.

In the present context the expression "specific cysteins which are replaced by a different amino acid" refers to cysteine residues, which contribute to the disulfide the formation of formation and to the new disulfide bonds not occurring in natural BMPs.

DRAWINGS

The patent or application file contains at least one drawing executed in color. Copies of this patent or patent application publication with color drawing will be provided by the Office upon request and payment of the necessary fee.

FIG. 1 shows the results obtained and the structure of inhBMP-4 mutants used for the reduction of the ALP activity in MC3T3-E1 cells. In panel A the ALP activity of the MC3T3-E1 cells treated with the indicated proteins is given. In panel B the schematic view of the structure of some of the constructs of the invention is shown (N-terminus to the left).

DETAILED DESCRIPTION OF THE INVENTION

The present invention is based on the development of a new generation of inhibitors of bone formation derived from the primary sequence of a BMP, exemplified here by a BMP-4, mutant consisting of the region involved in the formation of finger 2 including the wrist epitope of BMP-4 (BMP-4 mutant 1 of Finnish Patent Application 20011478). An improvement of the novel mutants of the present invention is that by the use of a part of the BMP sequence the remaining primary sequence cannot fold to an osteoinductive folding variant as it theoretically could be the case for mature BMP monomers. Thus the mutants of the present invention are essentially safer when used in therapy. The mutants of the present invention, however, reduce the alkaline phosphatase activity in MC3T3-E1 cells to a level seen after the application of a 1:1 mixture of inhBMP-2 and -4 monomers, i.e. are as effective as the previously disclosed inhibitors of the bone formation. Additionally, the mutants of the present invention are capable of forming new disulfide bonds, which are not present in natural BMPs.

In order to further study the cellular response to BMP-4 mutant 1 and the site of interaction, the five cysteines in BMP-4 mutant 1, namely C49 at the N-terminus, C80 and C81 in the middle, and C113/115 at the C-terminus, were changed to alanine residues with site-directed mutagenesis and the inhibitory effect of resulting mutants was evaluated using the murine osteoblastic cell line MC3T-E1. This cell line is frequently used to study BMP inhibitors at the cellular level, because these cells produce endogenous BMP-2 and BMP-4 and differentiate autocrine into mature osteoblasts under their influence (Natsume, T., et al., *J. Biol. Chem.* 272 (1997) 11535-11540). This process can easily be monitored by the increase in alkaline phosphatase (ALP) activity.

Figure 1:
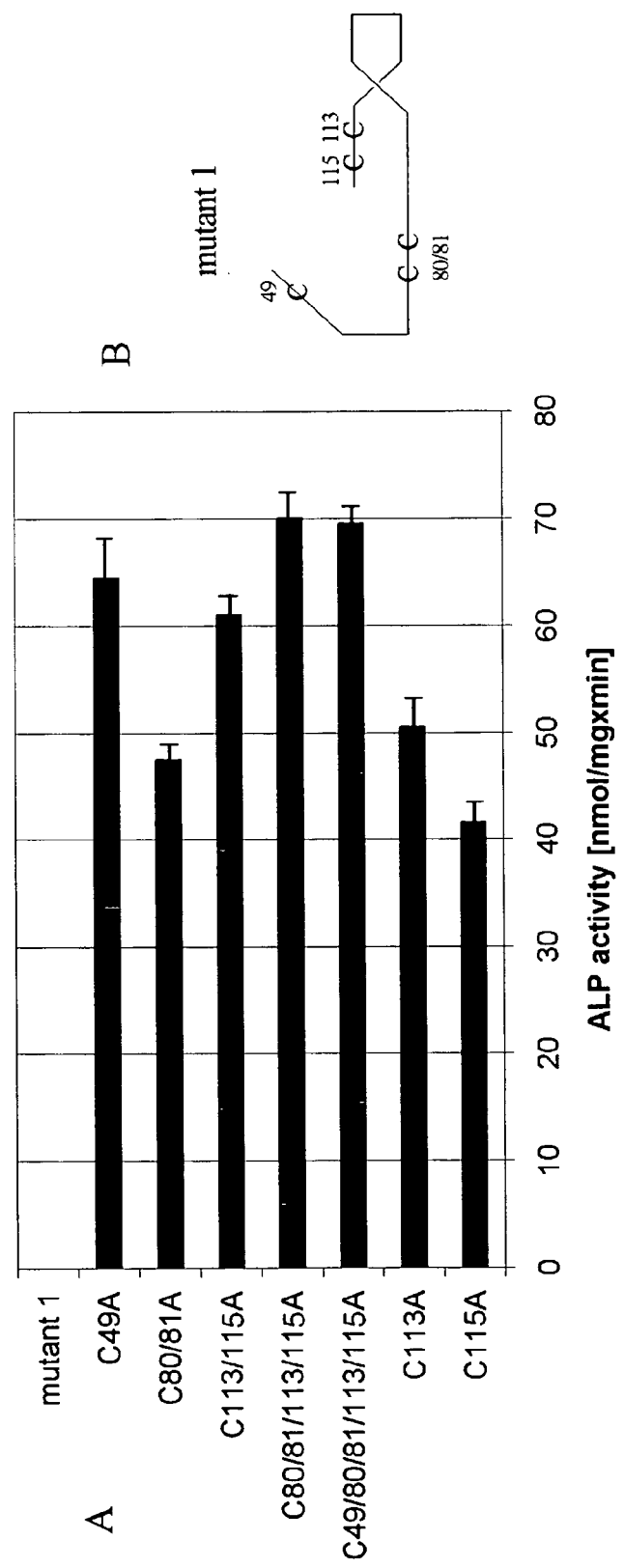

It was found that the exchange C80/81A, C113A and C115A had essentially no effect or had an improved effect (C115) on the inhibitory potential of mutant 1 but exchange C49A and C113/115 weakened the inhibitory potential of mutant 1 (FIG. 1). This indicates that C49 and C113 or C115 are indispensable for inhibition and, similar to osBMP, that the overall folding thereof and mutant 1 is determined by the position of cysteines and the formation of disulfide bridges. An unexpected result was that mutant 1 C115A is a better inhibitor than mutant 1 C 113A (p<0.01, n 16), although the naturally occurring disulfide bridge derived from the other members of the BMP family is between C49 and C115. This indicates that effective inhibitors for the BMPs depend not only on the lack of disulfide formation as shown earlier (Weber, F., et al., supra) but also on the formation of disulfide bonds, which do not occur in natural BMPs.

Figure 2:
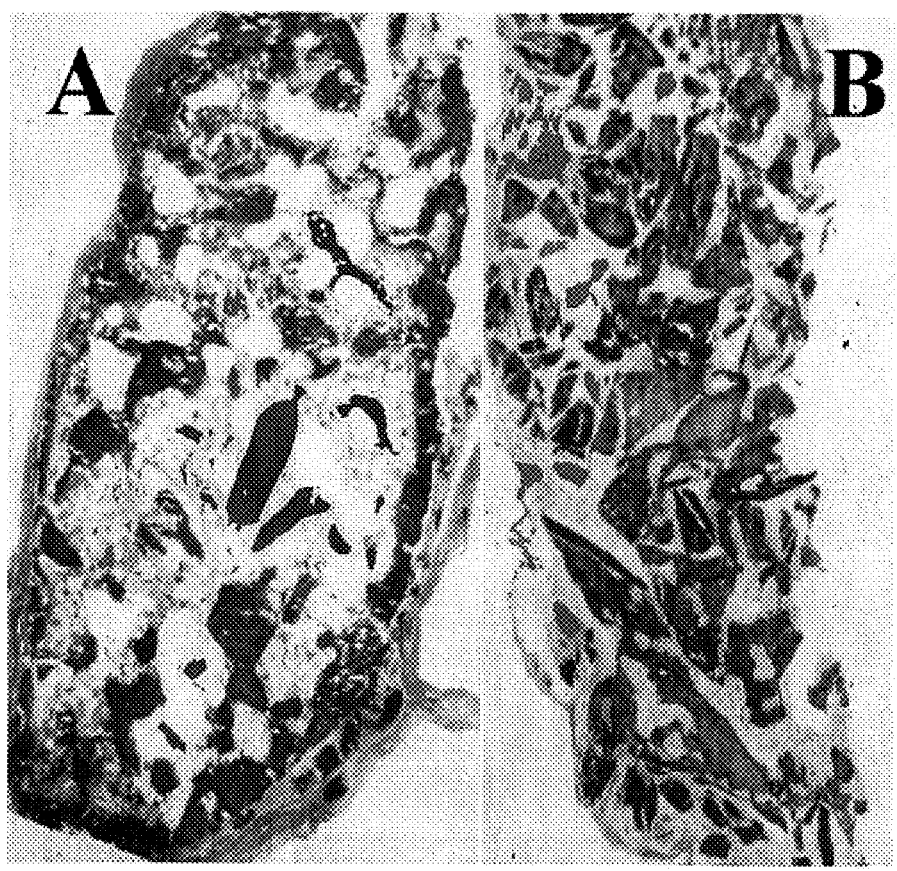
FIG. 2 shows the histological effect of mutant 1 C115A of the present invention.
Figure 3:
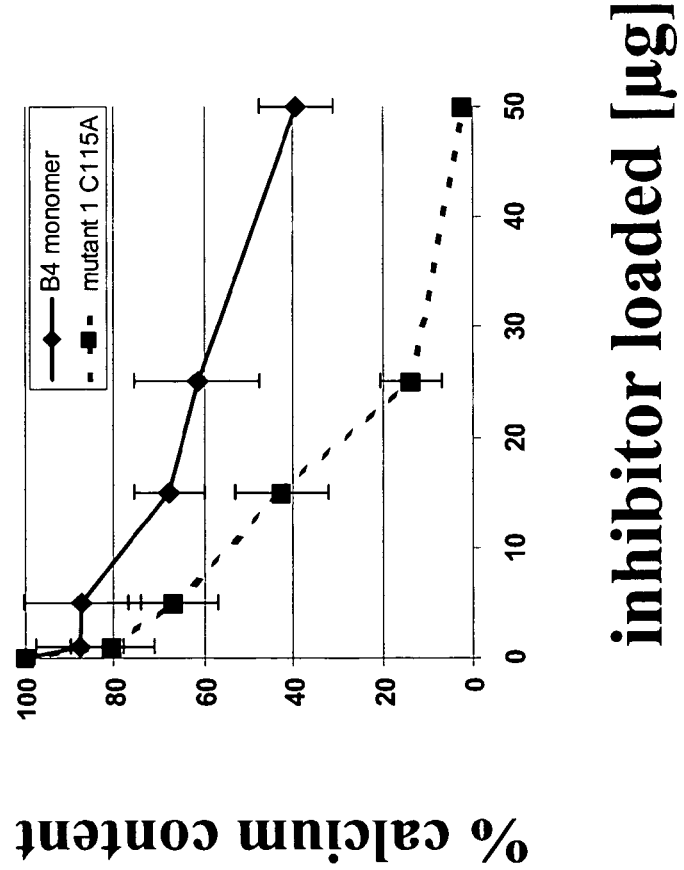
FIG. 3 shows a dose-dependent increase of osteoinhibition.

Next, some of the constructs were tested in the most frequently used in vivo model for HO, which involves the subcutaneous implantation of demineralized bone in rats to mimic heterotopic ossification (DiCesare, P. E., et al., *J. Orthop. Res.* 9 (1991) 855-861; O'Connor, J. P., *Clin. Orthop.* 346 (1998) 71-80). Constructs capable of decreasing the ALP activity in the MC3T3 E1 cells also reduced the calcium content of implants of the demineralized bone. That the calcium content in the implants reflects ossification was evaluated for all implants by means of Goldner-trichrome stained histosections (FIG. 2). In order to compare the effect of different constructs on osteoinhibition, the dose dependency of the inhibitor loading on the calcium content in implants was also determined. As shown in FIG. 3, increasing amounts of the inhibitor decrease the calcium content in the implant. The dose response curve of mutant 1 (data not shown) and mutant 1 C115A showed no significant difference. However, as evident from FIG. 3, mutant 1 C115A is more effective in inhibiting bone formation than BMP-4 monomer. At a dosage of 15 μg of protein the difference between mutant 1 C115A and BMP-4 monomer in lowering the calcium content is significant ($P>0.02$). Taken into account that the molecular weight of mutant 1 C115A is ⅔ of that of mature BMP-4 monomer, the former is even more effective, because the calcium content achieved by the application of 25 of mutant 1 C115A is lower than that achieved by 50 μg of BMP-4 monomer ($p<0.01$).

The BMP mutants of the present invention consisting of the region involved in the formation of finger 2 including the wrist epitope of the BMP are simple proteins for use in clinical applications to counteract the effects of the BMPs in HO by binding to a specific receptor. A representative of the mutants of the invention, BMP-4 mutant 1 C115A, was tested in vivo in the same model used for the evaluation of non-steroidal anti-inflammatory drugs. Indomethacin, one representative of these drugs, was shown to reduce the calcium content in implants of demineralized bone by 80%, if pre-treatment followed by a daily administration occurred (DiCesare, P. E., et al., supra). However, fifty micrograms of mutant 1 C115A reduced calcium contents by 98%, although it was administered only once locally and at the time point of osteoinduction. Thus, mutant C115A is more effective than indomethacin and could be used as a routine HO prophylaxis to be applied shortly after induction of ossification by a hip surgery or accidentally-induced ossification.

The novel mutants of the invention can be used as therapeutic agents in preventing the formation of new bone individually or in a suitable combination. BMP-4 mutants of the invention are preferred when used individually. Preferred combinations of mutants of the invention are combinations of a mutant based on BMP-4 with other BMP mutants, such as a mutant based on BMP-2.

The pharmaceutical compositions of the invention contain a mutant or mutants of the invention with a suitable carrier. Suitable carriers include those described in Finnish Patent Application 20011478, as applicable.

The invention is illustrated by the following examples, which are given only for illustrative purposes.

For statistical analysis, Student's T-test was implemented by a commercially available software package (SSPE, Chicago, Ill.). All values are represented as means+standard error of the mean.

EXAMPLE 1

Preparation of BMP-4 Mutants

For the preparation of BMP-4 mutants of the invention, the following procedures were used. In a first step, mature BMP-4 expression constructs and deletion mutant 1 were generated by PCR with respective cDNAs as templates in accordance with Finnish Patent Application 20011478. Briefly, a start codon as part of an Nde-restriction site was introduced by a PCR reaction as disclosed by Weber, F., et al. (*Cell Mol. Life Sci.* 54 (1998) 751-759) in front of the mature BMP-4 sequence (Sequence Id. No. 1), which added an N-terminal extension of a single methionine to the mature sequence. Mutant 1 was created by the insertion of a start codon at a defined position. Site directed mutagenesis using the double stranded plasmid DNA of mutant 1 as a template was performed using the QuickChange™ (Stratagene, La Jolla, Calif., USA) site directed mutagenesis kit. The oligonucleotides were designed as described by Braman, J., et al. (*Methods Biol. Mol.* 57 (1996) 31-44) so that the cysteine codon to be mutated was replaced by a codon for alanine, which was located in the middle of the designed oligonucleotide primer and flanked by a sufficient template sequence towards the 5-prime and the 3-prime end. A sense and antisense of the oligonucleotide containing the alanine codon was used in a PCR reaction with mutant 1 plasmid as a template.

Following the PCR reaction the template was digested by the methylation specific endonuclease Dpn I, and the remaining newly synthesized DNA was transformed into *Escherichia coli* cells. All resulting clones were sequenced prior to expression. The presence of an Nde restriction site in all clones allowed cloning into the pET23b+expression vector (Studier et al., *Methods Enzymol.* 185 (1990) 60-89) used for the transformation of *Escherichia Coli* strain BL21 (DE3). The cells were grown to an optical density of 0.6 (at 600 nm), induced by the addition of isopropyl 13-D-thiogalactopyranoside to a final concentration of 0.4 mM, and harvested 3 h after induction by centrifugation at 5000×g. The pellet was stored overnight at −80° C. After thawing the cells were re-suspended in 20 mM Tris-HCl, pH 7.9, 0.5 M NaCl, 5 mM imidazole, and lysed by three passages through a French pressure cell at 20,000 psi. After centrifugation, BMPs were present in the pellet.

To produce inhBMP-4, the pellet was dissolved in the same buffer as before with the addition of 6 M urea and incubated on a turning wheel for seven days at 4° C. Insoluble material was removed by centrifugation at 15,000×g for 30 min, and the supernatant applied to an affinity column (Chelating HP, 5 ml HiTrap®, Pharmacia Biotech), and eluted with 1 M imidazole in the same buffer. BMP-4 mutants were treated with dithiotreitol (a final concentration of 10 mM), subjected to a gel filtration (HiLoad® Superdex®) 200, Pharmacia Biotech, 1.6 cm×60 cm; 124 ml) with TU (50 mM Tris, pH 8, 6 M urea) as the water phase and the final products were stored in TU at 4° C. The protein concentration was determined with a Coomassie protein assay reagent (Pierce, II, USA).

EXAMPLE 2

Inhibitory Effects of the Mutants of the Invention at the Cellular Level

The murine osteoblastic cell line MC3T3-E1 was used to study inhibitory effects of the mutants of the invention at the cellular level. MC3T3-E1 cells were grown in an alpha-modified Minimum Essential Medium (Life Technologies, Inc., Grand Island, N.Y. USA) containing 10% fetal calf serum (Life Technologies, Inc.), 50 μg/ml gentamycin, and 50 μg/ml ascorbic acid. To examine the biological activity of BMPs, $1\times10^5$ cells per well were plated in 6-well plates and 1 μg of the protein/ml added subsequently. Medium exchange was performed after 3 days and alkaline phosphatase was determined on day 6. The cells were washed 3 times with phosphate buffered saline, and the cells from a single well were combined in 0.5 ml of lysis buffer (0.56 M 2-amino-2-methyl-propane-1-ol, pH 10) and homogenized by an omni-mixer. 200 μl of the cell lysate were mixed with 200 μl of lysis buffer supplemented with 20 mM p-nitrophenylphosphate and 4 mM $MgCl_2$ at 4° C.

The alkaline phosphatase activity was determined according to Lowry, O. et al. (*J. Biol. Chem.* 207 (1954) 19-37). p-nitrophenol liberated was converted to p-nitrophenylate by adding 400 μl of 1 M NaOH, which was quantitated by measuring the absorbance at 410 nm (epsilon=17500/molx cm). The alkaline phosphatase activity was normalized to total protein and expressed as nmol nitrophenylate generated per min per mg protein.

The alkaline phosphatase activity of the MC3T3 E1 cells treated with different BMP-4 mutants derived from mutant 1 is shown in FIG. 1. The schematic drawing to the right indicates the location of the cysteines in mutant 1. All values represent eight measurements and are given as means±standard error of the mean. As evident from FIG. 1, when cysteines at positions 80/81, 113 and 115 were replaced with alanine, the inhibitory potential of mutant 1 retained or improved (mutant 1 C115A). However, when the exchanges C49A and C113/115 were performed, the inhibitory potential of mutant 1 disappeared. Cysteines at positions 49, 113 or 115 are thus critical for inhibition.

EXAMPLE 3

Inhibition of Heterotopic Ossification Induced by Demineralized Bone

To determine the effect of the BMP mutants of the invention on ossification, demineralized bone powder was prepared from rat long bones essentially as described by Muthukumaran, N., et al., *Collagen Rel. Res.* 8 1988) 433-441. To produce inactivated bone collagen, demineralized bone material was extracted with 4 M guanidine hydrochloride (Sampath, T. K. and Reddi, A. H., *Proc. Natl. Acad. Sci. USA* 78 (1981) 7599-7603). The procedure for loading proteins was as follows: 25 mg of the material was weighted into a microcentrifuge tube and the protein was dissolved in 120 μl of 0.05 mM HCl containing 0.5 mg chondroitin sulfate. The control was prepared accordingly without the protein. After incubation at room temperature for one hour, 0.3 ml of rat-tail collagen (2 mg/ml in 0.1% acetic acid) was added to the carrier material, mixed by vortexing and then incubated for another 30 min. The loaded material was then mixed with 1.1 ml of EtOH (stored at −80° C.) and transferred to a −80° C. freezer for 1 h. The suspension was centrifuged for 30 min at 4° C., the supernatant removed and the pellet washed three times with 85% EtOH (−20° C.). The final pellet was formed in a 1 ml syringe and dried under a sterile hood over night.

Dried pellets were implanted subcutaneously in the thoracic region of anaethetized Sprague-Dawley rats weighing between 200 and 300 g and one pellet was implanted on each side of the thorax.

Bone formation was measured by the quantitation of the calcium content, which reflects the induction of bone formation as shown by Hammonds, R. G. (*Molecular Endocrinology* 4 (1990) 149-155). After excision the entire implant was weighted and divided in two. One part of the implant was weighted and homogenized with an omni-mixer (Waterbury, Conn., USA) in 1.5 ml of 3 mM $NaHCO_3$, 150 mM NaCl. After centrifugation (1000×g 15 min), the supernatant was used for alkaline phosphatase (ALP) determination and the pellet was re-suspended three times with 1 ml of 10 mM Tris-HCl, pH 7, and mixed at room temperature for 1 h. After the final wash, the pellets were extracted overnight with 1 ml 0.5 M HCl. The calcium content in the extract was measured by atomic absorption spectroscopy.

The results for BMP-4 monomer, mutant 1, mutant 1 C115A and mutant 1 C47+113A, which are shown in Table 1, clearly indicate the superiority of mutant 1 C115A.

TABLE 1

| Construct | B4 monomer | Mutant 1 | Mutant 1 C115A | Mutant 1 C47-113A |
|---|---|---|---|---|
| mean ± SD | 49.9 ± 15.1 | 8.9 ± 2.8 | 2.0 ± 0.9 | 77.2 ± 9.1 |

Dose-dependent increase of osteoinhibition of a mutant of the invention is shown in FIG. 3. Demineralized bone was loaded with increasing amounts (1-50 μg) of mutant 1 C115A or inhBMP-4 monomer. After 21 days the percentage of the calcium content in the probe in relation to unloaded implant was determined. The results are given as the mean±standard error of the mean of four animals. The dose of the mutant of the invention needed for inhibition was dose-dependent and, significantly, lower than that of the monomer.

Most of the implants were examined histologically, in which case they were fixed and then embedded in poly (methyl-methacrylate). Histological sections 4.5 μm thick were prepared and stained with Goldner-Trichrome and toluidine blue stains (Sheehan, D. and Hrapchak, B., in *Theory and Practice of Histotechnology*, Ed. the C. V. Mosby Company, 1980). The stained sections were examined for bone formation, cell type, morphology, and stromal details using bright-lighted microscopy.

The histological effect of 50 micrograms of mutant 1 C115A is shown in FIG. 2. With the unloaded implant an ossicle has formed consisting of new bone (green) and bone marrow (FIG. 2*a*). With mutant 1 C115A most of the demineralized bone is still present (red) but no formation of new bone (green) has occurred (FIG. 2*b*).

The invention claimed is:

1. A method of inhibiting heterotopic ossification in an individual in need of such treatment comprising
administering to the individual an effective therapeutic amount of a deletion mutant of a transforming growth factor β super-family member comprising a finger 2 region and a wrist epitope, wherein the deletion mutant has an ossification inhibiting mutation, wherein said deletion mutant comprises the carboxy terminal 69 amino acids of the mature bone morphogenetic protein 4 sequence of SEQ ID NO: 2, and wherein a cysteine residue corresponding to cysteine 115 of the mature bone morphogenetic protein 4 sequence SEQ ID NO: 2 is replaced by alanine in a manner to inhibit heterotopic ossification.

2. The method of claim 1 wherein the deletion mutant is administered locally to a site of induced ossification.

3. The method of claim 2 wherein the deletion mutant is administered daily.

4. The method of claim 1 wherein the deletion mutant is combined with a pharmaceutically acceptable carrier.

5. A method of inhibiting undesirable bone formation in an individual in need of such treatment comprising
administering to the individual an effective therapeutic amount of a deletion mutant of a transforming growth factor β super-family member comprising a finger 2 region and a wrist epitope, wherein the deletion mutant has an ossification inhibiting mutation, wherein said deletion mutant comprises the carboxy terminal 69 amino acids of the mature bone morphogenetic protein 4 sequence of SEQ ID NO: 2, and wherein a cysteine residue corresponding to cysteine 115 of the mature bone morphogenetic protein 4 sequence SEQ ID NO: 2 is replaced by alanine in a manner to inhibit undesirable bone formation.

6. The method of claim 5 wherein the deletion mutant is administered to an ectopic site.

7. The method of claim 5 wherein the deletion mutant is administered daily.

8. The method of claim 5 wherein the deletion mutant is combined with a pharmaceutically acceptable carrier.

9. A method of inhibiting the growth of bone forming lesions in an individual in need of such treatment comprising administering to the individual an effective therapeutic amount of a deletion mutant of a transforming growth factor β super-family member comprising a finger 2 region and a wrist epitope, wherein the deletion mutant has an ossification inhibiting mutation, wherein said deletion mutant comprises the carboxy terminal 69 amino acids of the mature bone morphogenetic protein 4 sequence of SEQ ID NO: 2, and wherein a cysteine residue corresponding to cysteine 115 of the mature bone morphogenetic protein 4 sequence SEQ ID NO: 2 is replaced by alanine in a manner to reduce the bone forming lesions.

10. The method of claim 9 wherein the deletion mutant is administered to a site including bone forming lesions.

11. The method of claim 10 wherein the deletion mutant is administered daily.

12. The method of claim 9 wherein the deletion mutant is combined with a pharmaceutically acceptable carrier.

* * * * *

SEQUENCE LISTING

<160> NUMBER OF SEQ ID NOS: 2

<210> SEQ ID NO 1
<211> LENGTH: 349
<212> TYPE: DNA
<213> ORGANISM: Homo sapiens

<400> SEQUENCE: 1

```
agccctaagc atcactcaca gcgggccagg aagaagaata agaactgccg gcgccactcg      60
ctctatgtgg acttcagcga tgtgggctgg aatgactgga ttgtggcccc accaggctac     120
caggccttct actgccatgg ggactgcccc tttccactgg ctgaccacct caactcaacc     180
aaccatgcca ttgtgcagac cctggtcaat tctgtcaatt ccagtatccc caaagcctgt     240
tgtgtgccca ctgaactgag tgccatctcc atgctgtacc tggatgagta tgataaggtg     300
gtactgaaaa attatcagga gatggtagta gagggatgtg ggtgccgct                 349
```

<210> SEQ ID NO 2
<211> LENGTH: 116
<212> TYPE: PRT
<213> ORGANISM: Homo sapiens

<400> SEQUENCE: 2

```
Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
            115
```